United States Patent [19]

Majeed et al.

[11] Patent Number: 5,536,506
[45] Date of Patent: Jul. 16, 1996

[54] USE OF PIPERINE TO INCREASE THE BIOAVAILABILITY OF NUTRITIONAL COMPOUNDS

[75] Inventors: Muhammed Majeed; Vladimir Badmaev, both of Piscataway, N.J.; R. Rajendran, Bangalore, Ind.

[73] Assignee: Sabinsa Corporation, Piscataway, N.J.

[21] Appl. No.: 393,738

[22] Filed: Feb. 24, 1995

[51] Int. Cl.$^6$ .............................. A61F 2/02; A61F 6/06; A61K 9/70; A61K 9/48
[52] U.S. Cl. .................. 424/464; 424/195.1; 424/423; 424/430; 424/434; 424/443; 424/451
[58] Field of Search .................. 424/195.1, 423, 424/430, 434, 443, 451, 464

[56] References Cited

U.S. PATENT DOCUMENTS 4,284,657  8/1981  Stanton .................. 426/651

OTHER PUBLICATIONS

Wood et al., "Piperine determination in pepper (Piper nigrum L) and its oleoresins—a reversed phase high-performance liquid chromatographic method", Overseas Dev. Nat. Resource Inst., Flavour Fragrance J., 3(2), 55–64, (1988.

Kawada et al., "Rapid Communication", *Proceedings of the Society for Experimental Biology and Medicine*, 188, 229–233 (1988).

Bano et al., "Effect of piperine on bioavailability and pharmacokinetics of propranolol and theophylline in healthy volunteers", *Eur. J. Clin. Pharmacol* (1991) 41:615–617.

Bano et al,. "The Effect of Piperine on Pharmacokinetics of Phenytoin in Healthy Volunteers", *Planta Medica*, vol. 17, 568–569 (1987).

Atal et al., "Biochemical Basis of Enhanced Drug Bioavailability by Piperine: Evidence that Piperine is a Potent Inhibitor of Drug Metabolism", *Journal of Pharmacol. & Experimental Therapeutics*, vol. 232, No. 1, (1985).

Zutshi et al., "Influence of Piperine on Rifampicin Blood Levels In Patients of Pulmonary Tuberculosis", *JAPI*, (1985) vol. 33, No. 3.

Dahanukar et al., "Influence of Trikatu Powder on Rifampicin Bioavailability", *Indian Drugs*, Jul. 1983, 402–404.

Atal et al., "Scientific Evidence on the Role of Ayurvedic Herbals on Bioavailability of Drugs", *Short Communication*, (1980).

*Primary Examiner*—Carlos Azpuru
*Attorney, Agent, or Firm*—Nikaido, Marmelstein, Murray & Oram

[57] ABSTRACT

A new composition and method for the improvement of gastrointestinal absorption and systemic utilization of nutrients and nutritional supplements, wherein the composition comprises an extract from the fruit of Piper containing a minimum of 98% of pure alkaloid piperine. The method comprises oral, topical, or parenteral administration of the compositions of the invention. A new process for the extraction and purification of piperine is also disclosed.

28 Claims, 3 Drawing Sheets

1

USE OF PIPERINE TO INCREASE THE BIOAVAILABILITY OF NUTRITIONAL COMPOUNDS

BACKGROUND OF THE INVENTION

1. Field of the Invention

The fifty percent increase in life expectancy of Americans from 1930 to 1980 can, in part, be attributed to the improvement in nutrition in the United States during that period. However, the situation today remains far from ideal, since six out of ten of the leading causes of death in this county, including heart attack, cancer, cirrhosis of the liver, and diabetes, are linked to diet. It becomes increasingly obvious that many of those diseases could be prevented with a well balanced diet and efficient nutritional supplementation with certain vitamins and minerals.

The problem is particularly severe in older Americans. Approximately 30 percent of older Americans do not get the dietary requirements of all the essential nutrients. The hazards of food-drug interactions in depleting essential nutrients are well recognized. It is unavoidable that old age calls for increased use of medications. For example, use of certain antibiotics decreases absorption of calcium and iron, while EDTA chelation therapy decreases absorption of zinc, iron, copper, and magnesium.

In addition, many foods which increase the risk of cancer and cardiovascular disease have to be eliminated from the diet, which further depletes the sources of essential nutrients. For example, excellent sources of vitamin B and vitamin D, such as red meat, liver, egg yolk, cheese and dairy products, have to be limited because of their high cholesterol content.

Limited menu also causes a depletion of essential amino acids, such as tryptophan which is important precursor of neurotransmitters and may play a role in the prevention of brain deterioration with aging.

The availability of essential nutrients is further compromised by poor gastrointestinal absorption.

The traditional way to offset insufficient nutrient supplementation, insufficient gastrointestinal absorption and insufficient metabolic utilization of essential nutrients is to administer large doses of, e.g., vitamin and mineral supplements.

2. Description of Related Art

Documents describing ayurvedic medicine dating from the period between the seventh century B.C. and the sixth century A.D. describe "trikatu". Trikatu is a sanskrit word meaning three acrids, and refers to a combination of black pepper (Piper nigrum Linn.), long pepper (Piper longum Linn.) and ginger (Zingiber officinale Rosc.). In traditional ayurvedic medicine these drugs are essential ingredients of many prescriptions and formulations used for a wide range of diseases. Experimental evidence shows that the use of "trikatu", and its constituents individually as well as collectively, enhance the bioavailability of a number of drugs. In those studies carried out in animals as well as human volunteers, it was noted that the active component is piperine. Piperine, or mixtures containing piperine, have been shown to increase the efficacy, blood levels, and bioavailability of a number of drugs including ingredients of vasaka leaves (Bose, K. G., (1928) Pharmacopeia India, Bose Laboratories, Calcutta), vasicine (Atal et al., *Journal of Ethnopharmacology*, 4, 229–233 (1981)), spartein (Atal et al., ibid), sulfadiazine (Atal et al., ibid), rifampicin (Zutshi, U. et al. (1984) *Journal of the Association of Physicians of India*, 33, 223–224), phenytoin (Bano et al., Planta Medica, 1987, pp. 568–569), pentobarbitone (Majumdar, A. N. et al. (1990), *Indian Journal of Experimental Biology*, 28, 486–487), theophylline (Bano et al., Eur. J. Clin. Pharmacol. (1991) 41:615–617) and propranolol (ibid).

Piperine has also been added in multi-drug formulations for the treatment of tuberculosis and leprosy. A formulation containing rifampicin, pyrazinamide and isoniazid has been tested in human volunteers (Indian Patent No. 1232/DEL/89). For most drugs, the comparative levels and peak concentration of the drugs in the presence of piperine were higher. The applicability of these results to the development of anti-tuberculosis and anti-leprosy formulations, which are presently cost prohibitive in developing countries, is apparent. Bioavailability enhancement helps to lower dosage levels and shorten the treatment course.

The effect of piperine on the bioavailability of propranolol has also been studied. The chronic oral administration of the anti-hypertensive agent propranolol is frequently rendered difficult due to the fact that steady therapeutic levels of this drug are not achieved or maintained. In addition, large doses are needed to be administered for efficacy and this frequently causes side-effects. Piperine has been shown to enhance the bioavailability of this drug. Propranolol administered with piperine shows a significant increase in plasma levels of the drug, presumably due to decrease in metabolism by the liver.

Similar results have been obtained with piperine and vasicine, theophylline, and phenytoin. In summary, all of these examples clearly illustrate the role of piperine as a drug bioavailability enhancer. The combination of piperine with tested drugs is effective primarily due to higher plasma concentration and a longer stay of the drugs in the body. The reduced dose of highly toxic drugs and their enhanced efficacy is obviously desirable.

As noted above, the exact mechanism of drug bioavailability enhancement by piperine is unknown. Several studies indicate that piperine may act primarily by non-specifically inhibiting the mixed function oxidases systems. This slows down the process of metabolic biodegradation of the drug and enhances the bioavailability of the drug. In a detailed study of the interaction of piperine with enzymatic drug biotransforming reactions in jejunal epithelial cells and liver hepatocytes in vitro and in vivo, piperine appears to be a non-specific inhibitor of drug metabolism. Such results led the authors to speculate that piperine may find useful applications in successful drug therapy, and represent an important addition to the chemotherapists armory for the quantitative enhancement of drug bioavailability (Atal et al., The Journal of Pharmacology and Experimental Therapeutics, Vol. 232, pp. 258–262, 1985).

SUMMARY OF THE INVENTION

The principle of the present invention is to provide a mechanism which allows the extraction of additional nutritional value from less and fewer foods, by enhancing systemic bioavailability of the essential nutrients.

The metabolic pathways for a nutrient and drug are different in that a nutrient sustains basic metabolism, and physiological functions of the organism, while a drug is utilized as an adjunct to basic metabolism, to restore homeostasis to the physiological functions. This distinction allows one to understand the different mechanism of bioavailability of the present invention. One mechanism, as described by the prior art, is applicable primarily to sustain therapeutic levels of a drug in the organism. The other, as discussed by the present inventors, is applicable to increase absorption of nutrients and increase their metabolic utilization.

The invention has been intended primarily, but not exclusively, to increase the gastrointestinal absorption of nutrients and botanical compounds. This invention is intended in general to enhance the crossing-over of nutrients and botanical compounds through biological barriers such as, but not limited to, gastrointestinal epithelium, respiratory lining, genitourinary lining, blood brain barrier and skin.

Although not wishing to be limited to any mechanism of action, it is believed that the basic mechanism of the invention is two-fold: by affecting various active and passive transport mechanisms as described in detail below; and by causing the increase for the substrate demand due to enhanced metabolism at the cellular level. This latter mechanism is triggered when the compositions and method of the invention affect thermoregulation of the body, acting directly or indirectly through activation of thermoreceptors, which results in increased thermogenesis, or metabolic heat energy production and release. By affecting thermoreceptors, particularly in the skin and mucosa, the invention prevents thermal and non-thermal nociceptive stimuli being carried to spinal dorsal horn cells, and acts as a local and general anesthetic, by increasing threshold for the nociceptive stimuli.

The active ingredient of the present invention is prepared by a novel process which produces piperine of a purity greater than 98%.

DESCRIPTION OF THE PREFERRED EMBODIMENTS

Figure 1:
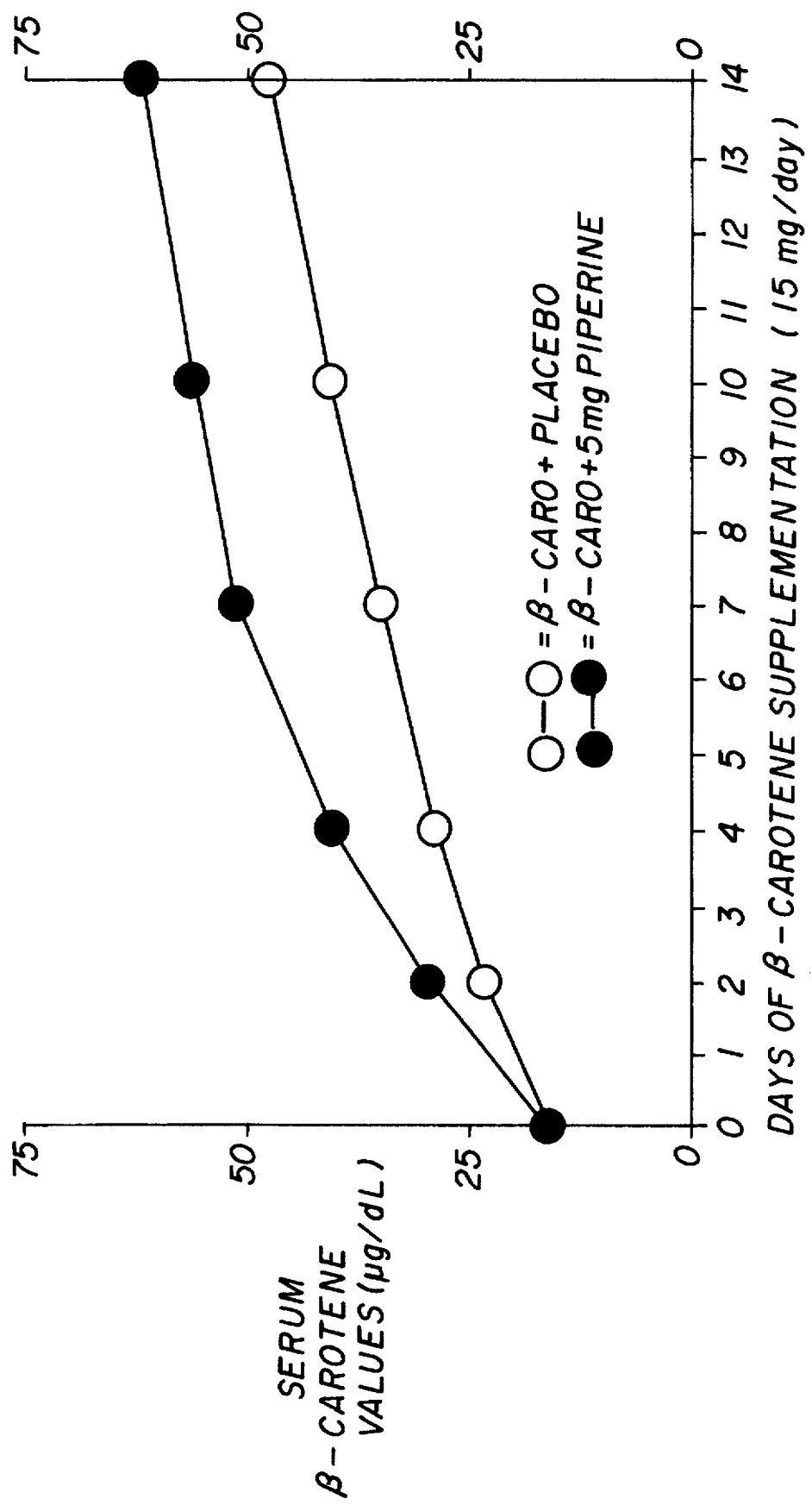
FIG. 1 shows the serum β-carotene levels on each day of treatment for patients treated with β-carotene and piperine versus β-carotene alone.

The present invention is directed to preparations and methods of using such preparations to improve the bioavailability of certain nutritional compounds. The compositions and methods of the present invention increase gastrointestinal absorption, improve crossing over through certain biological barriers such as respiratory lining, urinary lining, blood brain barrier and skin, and systemic utilization of certain nutrients and biological compounds.

The compositions of the invention also act by increasing thermogenesis. This mechanism is believed to be triggered by activation of thermoreceptors and release of catecholamines and/or direct action as beta 1, 2, 3-adrenoceptor agonist. Secretion of catecholamines can also be mediated by ATP via a P2-type purinergic receptors, and through a direct or indirect stimulation by the compositions of the invention of dopaminergic and serotinergic systems.

It is known that stimulation of beta-3 adrenoceptors results in increased thermogenesis, decrease in the amount of white adipose tissue without food intake being affected, increased levels of insulin receptors, and decreased levels of serum insulin and blood glucose. The invention may possess anti-obesity and anti-diabetic effects, which by themselves contribute to the mechanism of thermogenesis and the increase in lean body mass.

The anti-obesity and anti-diabetic effects of the present invention can be potentiated by using the compositions of the invention in combination with vanadium, in the form of vanadium organic and inorganic salts, both synthetic and naturally occurring.

The thermogenic effect of the invention may also be mediated by an increase in the activity of thyroid peroxidase, an important enzyme in thyroid hormone synthesis, an increase in the plasma levels of triiodothyronine (T3) and thyroxine (T4) with simultaneous increase in tissue oxygen uptake and increase in thermogenesis.

The thyrogenic and thermogenic effects of the present invention can be potentiated by using the compositions of the invention in combination with L-selenomethionine.

The compositions and methods of the present invention contain, as an essential ingredient, an extract from the fruit of piper nigrum comprising at least 98% piperine. Alternatively, the compositions may be prepared from an extract of the fruit of piper longum. Compositions of the present invention may also contain extract from roots of zingiber officinale, with active ingredients 6-gingerol and 6-shogoal. The compositions may be formulated with the extract from fruit of piper nigrum, extract from fruit of piper longum, and extract from roots of zingiber officinale combined in any weight ratio. Preferred weight ratios include 2:2:1, 1:1:1, 2:1:1, and 1:2:1.

When used in a preparation for oral administration, the piperine is used at a daily dose of 0.04–0.08 mg/kg of body weight, or, alternatively, a dose of about 4 mg piperine per 500 mg of nutrient, biological compound, or nutritional supplement for an average adult. When used as a preparation for topical or parenteral use to improve crossing over through a biological barrier, the compositions of the present invention contain, as an essential ingredient, 0.004–0.008 mg/kg of body weight of piperine, or alternatively a ratio of 0.4 mg of piperine per 500 mg of nutrient, biological compound, or nutritional supplement for an average adult.

The compositions of the present invention may also be used to affect thermoreceptors and prevent thermal and non-thermal noxious stimuli from being carried to the dorsal horn cells, which exerts local and general analgesic affects. The potentiation of analgesic affects is believed to be caused by increasing the absorption of the analgesic with which it is administered, and additionally, providing a synergistic or additive mechanism of analgesic action.

The compositions of the present invention improve gastrointestinal absorption and systemic utilization of the nutrients and nutritional supplements. Preferred embodiments elevate the maximum plasma concentration by 20–80% above the plasma concentration resulting when a regular supplement is taken alone.

The preparations of the present invention for improving gastrointestinal absorption and systemic utilization, may be made with any nutrient, biological compound, or nutritional supplement. Particularly preferred biological compounds include boswellin, curcumin, capsaicin, ashwagandha, ginkgo biloba, and aconitine. The compositions of the present invention to improve gastrointestinal absorption and systemic utilization may also include water soluble vitamins and fat soluble vitamins. Preferred water soluble vitamins include vitamin B1, vitamin B2, niacinamide, B6, B12, folic acid, and vitamin C. The absorption of water soluble vitamins is believed to work by preventing denaturing agents present in food from altering the protein-3-tetramer hydrophilic channels which facilitate gastrointestinal absorption of water soluble vitamins. In addition, the ability of piperine to enhance gastrointestinal absorption of vitamin B12 is believed to occur by stimulating synthesis and secretion of an intrinsic factor, a glycoprotein secreted by gastric parietal cells, which facilitates transport of vitamin B12 across the cellular membrane. The preparations of the present invention used to improve gastrointestinal absorption may also contain fat soluble vitamins. Preferred fat soluble vitamins are vitamins A, vitamin D, vitamin E, and vitamin K. In addition, carotenes such as alpha-carotene, beta-carotene and transbeta-carotene are believed to be subject to enhanced absorption due to a cholagogous mechanism which increases duodenal bile salts to emulsify fat soluble vitamins, and facilitate intracellular absorption via the mixed micelle system. The compositions of the invention may also include amino acids, particularly the essential amino acids lysine, isoleucine, leucine, threonine, valine, tryptophan, phenylalanine, and methionine. The amino acids are believed to be subject to enhanced gastrointestinal absorption by increasing the gamma-glutamyl cycle which facilitates transmembrane transport of amino acids.

As noted earlier, the nutritional status of older Americans is particularly problematic. Many antibiotics decrease the absorption of certain metallic and non-metallic minerals. To offset such losses, the compositions of the present invention may include essential minerals such as iodine, calcium, iron, zinc, copper, magnesium and potassium. Other metals such as vanadium, chromium, selenium and manganese may also be included in compositions of the present invention. It appears that the compositions of the present invention facilitate gastrointestinal absorption of these metallic compounds mainly by enhancing the active transport of these compounds across the membrane. In addition, the compositions of the present invention may prevent gastrointestinal absorption of certain dangerous heavy metals such as lead, mercury, and cadmium, and prevent systemic interference of the heavy metals with enzymatic functions. The compositions of the invention can form insoluble salts with mercury chloride, lead chloride and cadmium chloride and also protect sulfhydryl groups of enzymes from reacting with heavy metals.

The compounds of the present invention may also include antioxidants. Preferred antioxidants include vitamin A, vitamin C, vitamin E, alpha-carotene, transbeta-carotene, betacryptoxanthin, lycopene, lutein/zeaxanthin, pine bark bioflavanols complex, germanium, selenium, and zinc. The enhancement of antioxidant activity is believed to occur through enhanced systemic availability of antioxidant compounds through inhibition of lipid peroxidation and free radical formation. Preferred compositions of the present invention may include a variety of any of the above ingredients, which are particularly needed in a particular population.

Many of the nutrients, biological compounds and nutritional supplements which may be included in the compositions of the present invention are available commercially. Particularly, vitamin, mineral, amino acid and antioxidants are available commercially. The herbal compounds are generally used in powder form which is a dried ethanol extract of a particular plant. For example, Boswellic acid is from an ethanol extract of Boswellia serrata roots. Ginsenosides are from an ethanol extract of Ginseng roots. Withanaloids are from an ethanol extract of Whitania somnifera plant. Gingko flavinoids are from an ethanol extract of Gingko biloba plant. Curcuminoids are from ethanol extract of Cucuma longa plant. Pycnogenol is from an ethanol extract of Pinus pinaseter bark. Proanthocyanidins are from an ethanol extract of pine bark. Some of the herbal compounds are also available commercially from a variety of sources. The piperine in the invention may be produced by the new method of isolation of piperine. The compound obtained in this manner has the trademark name of Bioperine®. Alternatively, piperine may be provided by the prior art methods.

The following examples are not intended to be limiting in any way, but demonstrate some of the preferred embodiments of the present invention.

EXAMPLES

| NUTRITIONAL FORMULATIONS<br>Vitamin A tablets/capsules | |
|---|---|
| Example 1)<br>Formulation: Vitamin A tablets/capsules/softgels | |
| Vitamin A (Palmitate) | 10,000 IU |
| Piperine | 4 mg |
| Example 2)<br>Vitamins A & D tablets/capsules/softgels | |
| Vitamin A (Palmitate) | 10,000 IU |
| Vitamin D (Calciferol) | 400 IU |
| Piperine | 4 mg |
| Example 3)<br>Betacarotene capsules/softgels | |
| Betacarotene | 15 mg |
| Piperine | 4 mg |
| Example 4)<br>Curcumin Capsules | |
| Curcumin (min. 95% of curcuminoids) | 500 mg |
| Piperine | 5 mg |
| Example 5)<br>Boswellin Capsules | |
| Boswellia Serrata Extract<br>(65% Boswellic acid min.) | 320 mg |
| Piperine | 3 mg |
| Example 6)<br>Herbal capsules/tablets | |
| Formula A | |
| Valerian root | 100 mg |
| Chamomile (flower) | 100 mg |
| Passion Flower | 25 mg |
| Ginseng root powder | 50 mg |
| Skullcap | 25 mg |
| Nettle leaves | 25 mg |
| Piperine | 3 mg |
| Formula B | |
| Buchu leaves | 100 mg |
| Uva Ursi leaves | 25 mg |
| Celery seed | 25 mg |
| Juniper berries | 50 mg |
| Parsley leaves | 50 mg |
| Corn silk | 50 mg |
| Piperine | 4 mg |
| Formula C | |
| Echinacea root | 100 mg |
| Astragalus root | 100 mg |
| Barley leaves | 50 mg |
| Schizandra berries | 100 mg |
| Shiitake Mushroom | 50 mg |
| Piperine | 5 mg |
| Formula D | |
| Ginseng extract<br>(5% Ginsenosides) | 500 mg |

NUTRITIONAL FORMULATIONS
Vitamin A tablets/capsules

| | |
|---|---|
| Piperine | 5 mg |
| Formula E | |
| Ginseng extract | 250 mg |
| Ashwagandha extract (1% withanaloids) | 250 mg |
| Piperine | 5 mg |
| Formula F | |
| Gingko Biloba extract | 240 mg |
| (24% ginkoflavinoids) | |
| Piperine | 3 mg |
| Formula G | |
| Boswellia Serrata extract | 320 mg |
| Curcumin | 200 mg |
| Piperine | 5 mg |
| Formula H | |
| Boswellia Serrata extract | 320 mg |
| Capsaicin | 3 mg |
| Piperine | 4 mg |
| Example 7) | |
| Anti-oxidant tablets/capsules | |
| Formula A | |
| Vitamin C | 250 mg |
| Vitamin E | 100 IU |
| Vitamin A (Beta Carotene) | 10,000 IU |
| Selenium | 50 µg |
| (from L-Selenomethionine) | |
| Chromium | 50 µg |
| (Chromium Picolinate) | |
| Piperine | 4 mg |
| Formula B | |
| Pycnogenol | 30 mg |
| Piperine | 3 mg |
| Formula C | |
| Pine bark extract | 15 mg |
| Curcumin | 15 mg |
| Piperine | 3 mg |
| Formula D (softgel) | |
| Coenzyme $Q_{10}$ | 15 mg |
| Piperine | 3 mg |
| Formula E - Anti-oxidant beverage drink | |
| Vitamin C | 200 mg |
| Beta carotene | 15 mg |
| Vitamin E | 100 IU |
| Zinc (monomethionine) | 15 mg |
| Selenium (L-Selenomethionine) | 50 µg |
| Citrus bioflavanoid complex | 50 mg |
| Quercetin | 25 mg |
| Rutin | 25 mg |
| Hesperidin (Citrus) | 20 mg |
| Pycnogenol | 5 mg |
| Piperine | 2.5 mg |
| Example 8) | |
| Amino Acid Formulation | |
| L-Taurine | 200 mg |
| L-Carnitine | 100 mg |
| Piperine | 2.5 mg |
| Example 9) | |
| Vitamin B Complex | |
| Pantothenic Acid (Vitamin B5) | 200 mg |
| Niacinamide (Vitamin B5) | 125 mg |
| Pyridoxine HCL (Vitamin B6) | 75 mg |
| Thiamine (Vitamin B1) | 60 mg |
| Riboflavin (Vitamin B2) | 25 mg |
| Para-aminobenzoic acid (PABA) | 25 mg |
| Folic acid | 400 µg |
| Cobalamin (Vitamin B12) | 200 µg |
| Biotin | 100 µg |
| Piperine | 4 mg |
| Example 10) | |
| Multi Vitamin | |
| Vitamin A | 5,000 IU |
| Vitamin B1 | 1.5 mg |
| Vitamin B2 | 1.7 mg |
| Vitamin B6 | 2.0 mg |
| Niacinamide | 20 mg |
| Vitamin E | 30 IU |
| Vitamin B12 | 6 mg |
| Pantothenic Acid | 10 µg |
| Vitamin D | 400 IU |
| Vitamin C | 100 mg |
| Folic Acid | 400 µg |
| Biotin | 30 µg |
| Calcium | 200 mg |
| Magnesium | 400 mg |
| Iron | 18 mg |
| Iodine (Kelp) | 150 µg |
| Copper | 2 mg |
| Manganese | 2.5 mg |
| Potassium | 40 mg |
| Chromium | 25 mg |
| Selenium | 25 mg |
| Vitamin K1 | 25 mg |
| Piperine | 5 mg |
| Example 11) | |
| Hydroxycitric Acid | |
| Citrin ® | 500 mg |
| (Calcium salt of hydroxycitric acid) | |
| Piperine | 5 mg |

The above formulations and ingredients are examples, and are not intended to limit the invention in any way.

Example 12

The effect of Bioperine™ on β-carotene absorption and plasma concentration in humans.

The preliminary results of testing the following formulations:

Formula A—15 mg β-carotene (10% beadlets, 150 mg), 250 mg microcrystalline cellulose encapsulated in size 0 capsules.

Formula B—15 mg β-carotene (10% beadlets, 150 mg) 5 mg Bioperine™, 250 mg microcrystalline cellulose encapsulated in size 0 capsules.

Figure 2:
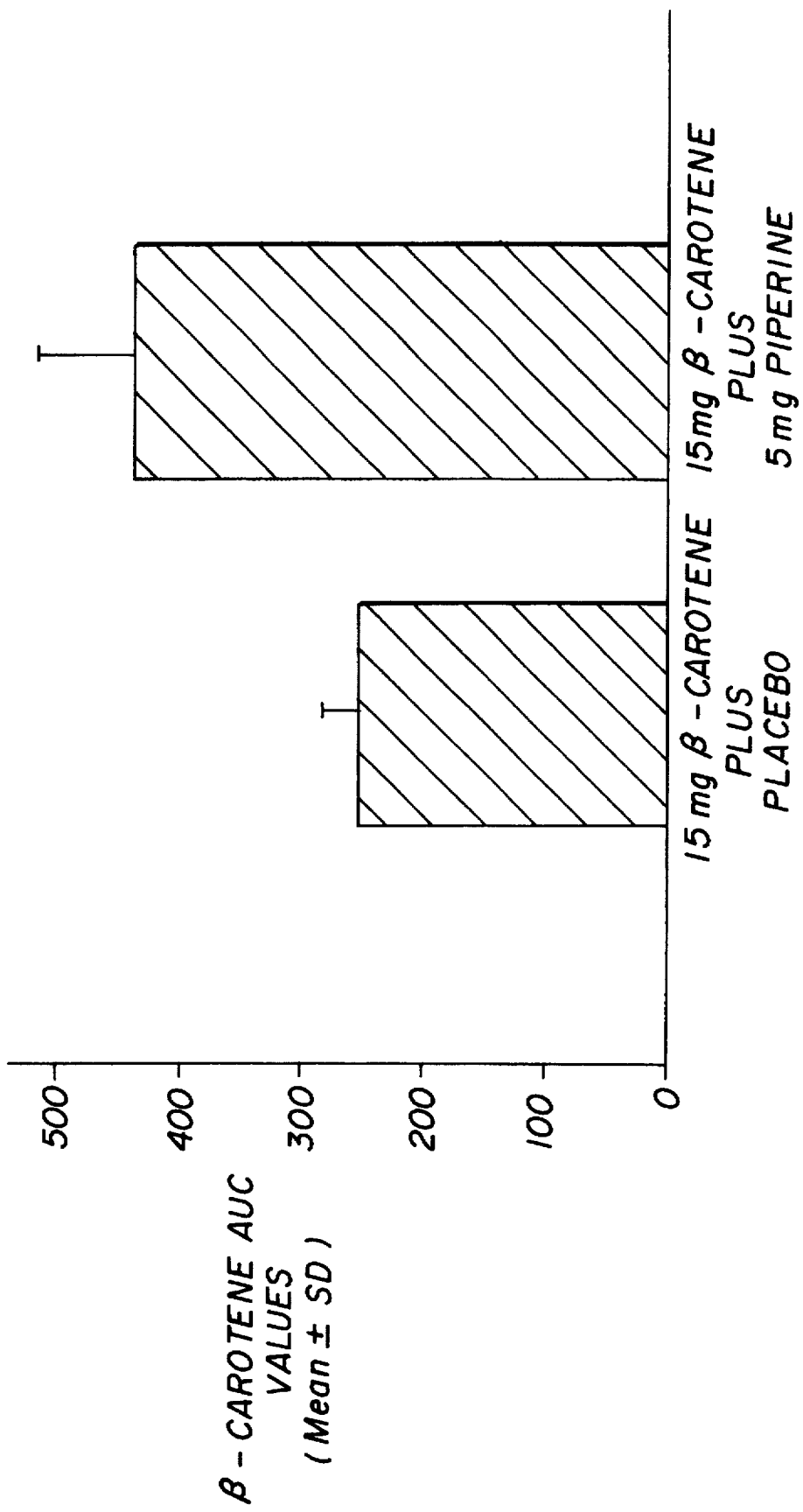
FIG. 2 shows the serum β-carotene levels for the entire treatment period for patients treated with β-carotene and piperine versus β-carotene alone.
Figure 3:
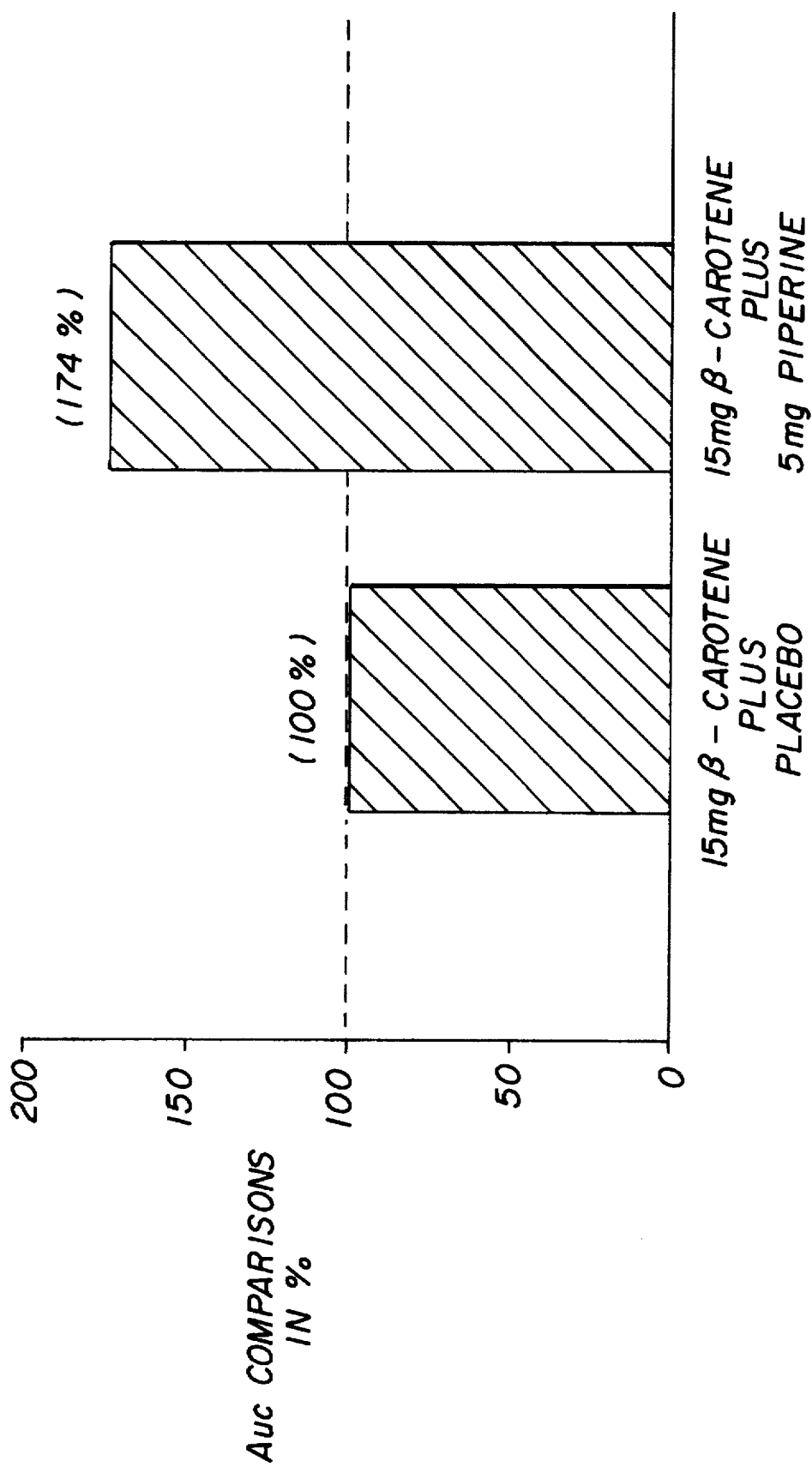
FIG. 3 shows the serum β-carotene levels for patients treated with β-carotene and piperins as a percentage of the serum levels of β-carotene for patients treated with β-carotene alone.

Results of this study demonstrate that the average baseline serum β-carotene, and retinol values of volunteers from the two formulation groups were not significantly different prior to the β-carotene supplementation period. However, after supplementation with β-carotene alone or β-carotene+Bioperine™ for 14 days, volunteers from the control group or group A (β-carotene alone) were found to have significantly smaller increases in serum β-carotene values than volunteers from experimental group or group B (β-carotene+Bioperine™) as determined by comparison of their mean area under the serum β-carotene curve from baseline through day 14. (FIG. 1, FIG. 2, FIG. 3).

Analysis of covariance was used to determine if the mean area under the serum β-carotene curve from baseline through day 14 of supplementation or the mean absolute changes in β-carotene values from baseline to day 14 of supplementation were affected by changes in retinol values from baseline to day 14. These analyses determined that changes in β-carotene values in groups A and B from day 0 to day 14 were not affected by serum retinol changes during this period.

In summary, these findings demonstrate that group B (β-carotene +Bioperine™) produces a significantly greater area under the serum β-carotene curve during 14 days of β-carotene supplementation than the control or group A (β-carotene alone). When mean absolute change from baseline level was used for comparison, group B also was found to produce significantly greater absolute changes than group A (controls).

Example 13

A preparation obtained in a unique manufacturing process.

Commercially available Black pepper oleoresin or Long pepper oleoresin is used as the source of piperine. Ground up Black pepper or Long pepper can also be used.

To a mixture of butanol and hexane (35 liters), 35 kg Black pepper oleoresin is added and heated to 40° C. The mixture is then cooled and filtered.

The precipitate is washed with Butanol/hexane mixture to obtain crude piperine.

The crude piperine is dissolved in methanol at 60° C. and treated with alumina and charcoal by stirring. It is then filtered and concentrated under vacuum to obtain a powder.

Bioperine™

Material thus prepared has the following specifications:
Color: Pale yellow crystalline powder Melting range: 128 degrees–131 degrees Celsius Assay: min. 98% pure piperine (by HPLC)

We claim:

1. A composition suitable for improving gastrointestinal absorption and systemic utilization of nutritional materials, subsequent increase in nutrient induced thermogenesis, and increase in lean body mass comprising at least one nutritional material in a nutritionally effective amount and an extract from the fruits of family Piperaceae comprising at least 98% of alkaloid piperine wherein the piperine is present in a therapeutically effective amount such that a daily dose consists of 0.004 to 0.08 mg/kg of body weight.

2. The composition of claim 1 wherein the piperine is extracted from the fruit of piper nigrum or black pepper.

3. The composition of claim 1 wherein the piperine is extracted from the fruit of piper longum.

4. The composition of claim 1, which contains additionally an extract from the root zingiber officinale.

5. The composition of claim 1 wherein the nutritional materials comprise one or more members selected from the group consisting of herbal extracts, water soluble vitamins, fat soluble vitamins, amino acids, minerals, anti-oxidants, and combinations containing two or more of the above nutritional materials.

6. The composition of claim 5 wherein the herbal extracts comprise one or more members selected from the group consisting of curcumin, boswellin, ashwagandha, ginkgo biloba, capsaicin, and aconitine.

7. The composition of claim 5 wherein the water soluble vitamins comprise one or more members selected from the group consisting of B1, B2, niacinamide, B6, B12, folic acid, and vitamin C.

8. The composition of claim 5 wherein the antioxidants comprise one or more members selected from the group consisting of vitamin A, vitamin C, vitamin E, alpha-carotene, transbetacarotene, betacryptoxanthin, lycopene, lutein/zeaxanthin, pine bark bioflavanols complex, germanium, selenium, and zinc.

9. The composition of claim 5 wherein the amino acids comprise one or more members selected from the group consisting of lysine, isoleucine, leucine, threonine, valine, tryptophan, phenylalanine, methionine, and L-selenomethionine.

10. The composition of claim 5 wherein the minerals comprise one or more members selected from the group consisting of calcium, iron, zinc, vanadium, selenium, chromium, iodine, potassium, manganese, copper, and magnesium.

11. The composition of claim 1 which contains an extract from the fruit of piper nigrum, an extract from the fruit of piper longum, and an extract from the root of zingiber officinale.

12. The composition of claim 1, suitable for oral administration, in a unit dose form of 0.04–0.08 mg/kg of body weight.

13. The composition of claim 1, suitable for oral administration which contains a unit dose of 4 mg of piperine per 500 mg of nutritional material.

14. The composition of claim 1, suitable for topical or parenteral use, containing the unit dose of 0.004–0.008 mg/kg of body weight.

15. The composition of claim 1, suitable for topical or parenteral use, containing the unit dose of 0.4 mg per 500 mg of nutritional material.

16. A method for improving gastrointestinal absorption and systemic utilization of nutritional materials, subsequent increase in nutrient induced thermogenesis, and increase in lean body mass; said method comprising administering to a subject in need thereof a composition containing at least one nutritional material in a nutritionally effective amount, and an extract from the fruit of piper comprising at least 98% of alkaloid piperine in a therapeutically effective amount such that a daily dose consists of 0.004 to 0.08 mg/kg of body weight.

17. The method of claim 16 wherein the piperine is extracted from the fruit of piper nigrum or black pepper.

18. The method of claim 16 wherein the piperine is extracted from the fruit of piper longum.

19. The method of claim 16, which contains additionally an extract from the root zingiber officinale.

20. The method of claim 16 wherein the nutritional materials comprise one or more members selected from the group consisting of herbal extracts, water soluble vitamins, fat soluble vitamins, amino acids, minerals, anti-oxidants, and combinations containing two or more of the above nutritional materials.

21. The method of claim 20 wherein the herbal extracts comprise one or more members selected from the group consisting of curcumin, boswellin, ashwagandha, ginkgo biloba, capsaicin, and aconitine.

22. The method of claim 20 wherein the water soluble vitamins comprise one or more members selected from the group consisting of B1, B2, niacinamide, B6, B12, folic acid, and vitamin C.

23. The method of claim 20 wherein the antioxidants comprise one or more members selected from the group consisting of vitamin A, vitamin C, vitamin E, alpha-carotene, transbetacarotene, betacryptoxanthin, lycopene, lutein/zeaxanthin, pine bark bioflavonals complex, germanium, selenium, and zinc.

24. The method of claim 20 wherein the amino acids comprise one or more members selected from the group consisting of lysine, isoleucine, leucine, threonine, valine, tryptophan, phenylalanine, methionine, and L-selenomethionine.

25. The method of claim 20 wherein the minerals comprise one or more members selected from the group consisting of calcium, iron, zinc, vanadium, selenium, chromium, iodine, potassium, manganese, copper, and magnesium.

26. The method of claim 16 which contains an extract from the fruit of piper nigrum, extract from the fruit of piper lungum, and extract from the root of zingiber officinale.

27. The method of claim 16 wherein the composition is administered orally.

28. The method of claim 16 wherein the composition is administered topically or parenterally.

* * * * *